United States Patent [19]

Natens et al.

[11] 4,004,216
[45] Jan. 18, 1977

[54] APPARATUS FOR DETECTING METALLIC PARTICLES IN A FLOW OF DIELECTRIC MEDIUM

[75] Inventors: Luc Yves Natens, Berchem; Jean Martha De Gueldre, Edegem, both of Belgium

[73] Assignee: AGFA-GEVAERT N.V., Mortsel, Belgium

[22] Filed: Mar. 17, 1975

[21] Appl. No.: 559,040

[30] Foreign Application Priority Data

Mar. 19, 1974 United Kingdom ............. 12167/74

[52] U.S. Cl. .................................................. 324/41
[51] Int. Cl.² ........................................ G01R 33/12
[58] Field of Search ....................... 324/41; 331/65

[56] References Cited
UNITED STATES PATENTS

| | | | |
|---|---|---|---|
| 2,958,037 | 10/1960 | Riede et al. | 324/41 |
| 3,103,655 | 9/1963 | Jones | 331/65 |
| 3,231,815 | 1/1966 | Spencer | 331/65 |
| 3,665,298 | 5/1972 | Geiger | 324/41 |

FOREIGN PATENTS OR APPLICATIONS 662,393   4/1963   Canada ................. 324/41

Primary Examiner—Robert J. Corcoran
Attorney, Agent, or Firm—William J. Daniel

[57] ABSTRACT

An apparatus for detecting the presence of metallic particles in a flow of dielectric material is based upon the principle of measuring the frequency shift of an oscillator upon passage of such a particle through the self induction coil forming part of said oscillator. Special arrangements are provided for rendering the magnetic field as uniformly as possible within the coil so that the magnitude of the signal is not subject to significant fluctuations whether the particle passes through the center of the self-induction coil or not.

12 Claims, 24 Drawing Figures

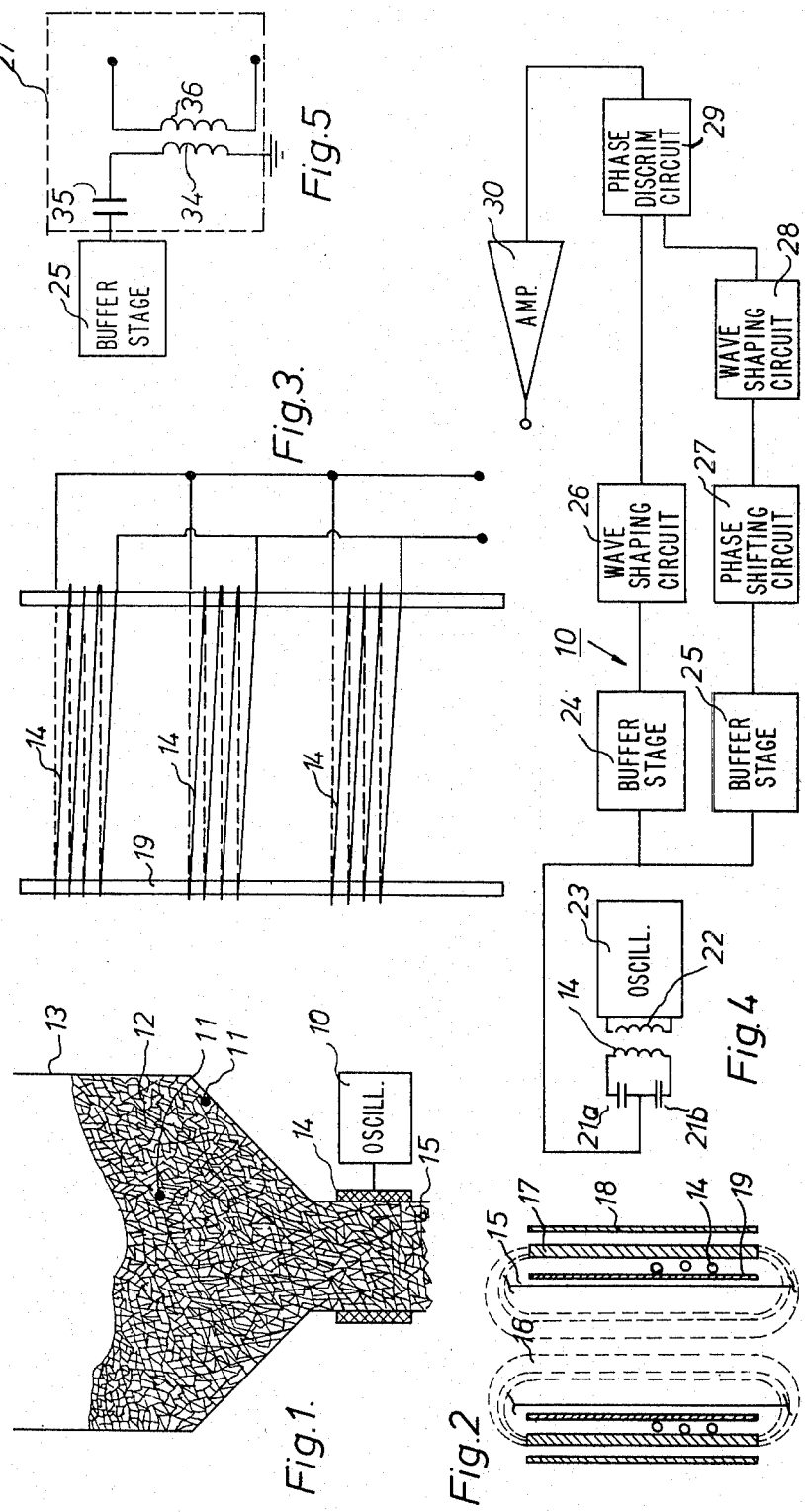

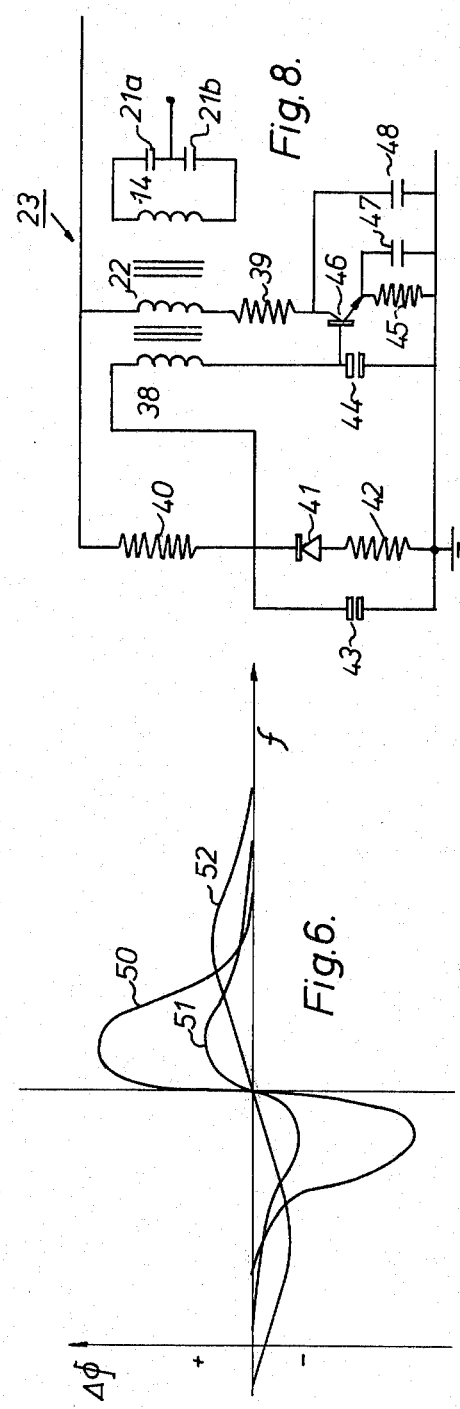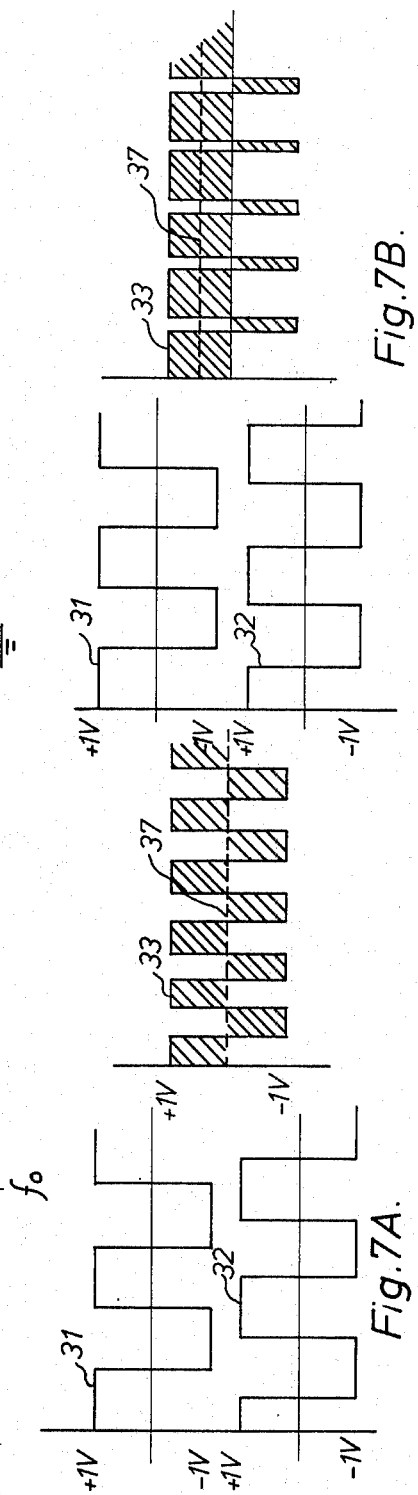

↕100mVolts

APPARATUS FOR DETECTING METALLIC PARTICLES IN A FLOW OF DIELECTRIC MEDIUM

This invention is concerned with detection apparatus, and more particularly with the detection of metallic particles in a dielectric space.

The invention is particularly intended for detecting metallic particles which might be present in a mass of polyester granulate prior to forwarding the latter to an extrusion installation.

The presence of such metallic particles in polyester granulate might be the cause of serious troubles or damage to the extruder screw or the die due to the non-deformability or the high deformation resistance of said particles and the relatively narrow spaces through which they would be forced.

A timely detection enables to take preventive measures such as stopping the extruder or emptying the hoppers in which the granulate is stocked and/or dried. Such preventive measures, although they have proved to be very costly, due to the unavoidable temporary interruption of production, are however outweighed by the costs of the production losses and the occasional damage to the extruder body, the extruder screw and/or the die caused by metallic particles which accidentally got mixed with the raw material.

Detection apparatus are already marketed, being based upon the phenomenon that the amplitude of the electrical voltage at resonant frequency of a parallel resonance circuit will undergo fluctuations when one of the constituent parts of said circuit is changed. In that particular apparatus, the self-induction coil is placed in the peripheral surface of a tube through which the polyester granulate flows so that the passage of a metallic particle past said coil influences the characteristics of the resonance circuit by acting on the configuration or the magnitude of the lines of magnetic force within said coil. The resulting fluctuations may be detected by a suitable amplitude detector, whereinafter the detected signals may be amplified in order to get sufficient power for energizing e.g. an alarm circuit.

A careful study of the transfer function of such parallel resonant circuit detector used in combination with an oscillator, the latter acting as a compensator for the unavoidable damping occurring in such circuit, reveals that amplitude detection strongly limits the general use of such detecting device.

Indeed, a noticeable disturbance of the lines of magnetic force within the self induction coil will only occur if bodies having a high coefficient of magnetic permeability and presenting at the same time sufficient eddy current losses are introduced in said coil. Such system will thus be capable of detecting magnetic iron particles, but will be less suitable for the detection of say, copper or brass, or non-magnetic stainless steel.

It is therefore an object of the invention to remedy the aforementioned drawbacks.

Another object of the invention is to provide a detection system for metallic particles of different shape and dimensions.

Other advantages of the apparatus according to the invention will becom evident in the course of this description.

According to the invention, there is provided: an apparatus for detecting the presence of metallic particles in a flow of dielectric medium, comprising:

— a tube through which the dielectric medium flows
— oscillator means oscillating at a given resonant frequency
— a parallel resonance circuit, capable to be excited by the electrical energy, emitted by said oscillator means, the self-induction coil of said parallel resonant circuit being arranged (preferably concentrically) around said tube and
— detector means, coupled with said parallel resonant circuit, and capable to detect changes of the frequency and/or phase of the signal in said parallel resonant circuit upon the passage of a metallic particle through said tube.

An apparatus as identified hereinbefore will be able to generate a signal which will depend on the change in phase difference between two signals, said phase difference being related to the disturbance of the magnetic field or the change of at least one of the parameters responsible for the creation of said magnetic field.

When considering a parallel resonant circuit comprising a self-induction coil, a capacitor and a resistor, the latter representing the resistive losses in said circuit, three cases must be considered when a foreign metallic particle is introduced into the center of the self-induction coil, in which the magnetic field is created.

When in the above case, a ferromagnetic particle is considered, the latter being introduced into the center of the sel-induction coil the average permeability of the magnetic meduim wil increase, so that the coefficient of self-inductance L will increase too, causing a decrease of the resonant frequency, the latter being defined by the square root of 1/LC, C being the capactiy of the capacitor placed in parallel with said self-induction coil L. Here the resistance R, being normally neglectable, has not been taken into consideration.

When the particle has highly electrically conducting properties, eddy currents of high amplitude will be induced in the body, causing a displacement or partial annihilation of the lines of the magnetic field which means that the coefficient of self-induction has decreased and that the resonant frequency has increased.

When finally the particle has poor conducting properties, the induced eddy currents will cause resistive losses in the material causing an increase of the damping the latter being defined by the expression $k = (1/2R)\sqrt{L/C}$. In this case the amplitude of the voltage at resonant frequency will be lowered, and by the fact that R may not be neglected anymore, the resonant frequency will increase.

Bearing the foregoing features in mind, the sensitivity of an apparatus which is capable to detect only changes in amplitude will be very high for ferromagnetic materials such as iron or steel, as due to the high permeability and the relatively high electrical resistance of the latter metals, a great number of lines of magnetic force will be absorbed and the resistive losses will increase. On the contrary the detection sensitivity will be low for electrical conductors, such as gold, silver, copper, etc. It may even occur that the sensitivity of the system becomes zero, because the quality factor Q of the circuit being equal to $R\sqrt{C/L}$ may remain unchanged when both R and L decrease, as it may be the case with some para- and diamagnetic substances such as e.g. iron.

In the three possible cases, mentioned hereinbefore, the resonant frequency of a parallel resonant circuit will thus be the parameter which will change when a metallic particle, whatever be its magnetic properties, is introduced into the self-induction coil of said parallel resonant circuit. To provide an apparatus, capable of detecting frequency changes is therefore a main object of the invention, which will be described in detail hereinafter with reference to the following drawings, in which:

FIG. 1 gives a schematic view of the location of an apparatus according to the invention, FIG. 2 is a cross-sectional view of the configuration of the magnetic field, FIG. 3 is a view of the configuration of the self-induction coil, FIG. 4 is a schematic diagram of the apparatus according to the invention, FIG. 5 is a schematic diagram of one coupling stage in the apparatus of FIG. 4, FIG. 6 illustrates the phase difference as a function of the frequency at the outlet of the coupling stage of FIG. 5.

FIGS. 7a and 7b illustrate the signal at the output of the apparatus of FIG. 4 at resonant frequency and at non-resonant frequency respectively, FIG. 8 gives a diagram view of the oscillator of the apparatus of FIG. 4, FIGS. 9a to 9e illustrate the output signal of the detecting apparatus with the resonant frequency equal to 200 kHz, for iron, stainless steel, brass, aluminum and copper respectively, FIGS. 10a to 10e illustrate the output signal of the detecting apparatus for the same metals as in FIGS. 9 at a resonant frequency of 100 kHz, FIGS. 11a to 11e illustrate the output signal of the detecting apparatus for the same metals as in FIGS. 9 at a resonant frequency of 100 kHz but with a supplementary field correction.

In FIG. 1 the general set-up of an apparatus 10 according to the invention is shown, which is intended for the detection of metallic particles 11 which may accidentally be present in a dielectric medium 12, such as polyester chips or granulate stocked in a hopper 13. To this end a self-induction coil 14 is provided around the outlet tube 15 of the hopper 13, which permits the detection of the particles 11 as these will vary the frequency and/or the amplitude of the magnetic field created in the tube by the self-induction coil when the latter forms a parallel resonant circuit in combination with a parallelly coupled capacitor (not shown).

The disturbance created by a moving particle 11 is transformed into an analogic electric signal which will serve to energize an alarm device after its amplification, so that precautionary measures may be taken such as stopping the extruder or emptying the hopper in which the polyester chips or granulate 12 fall prior to extrusion. One of the major problems one has to face is the creation of a magnetic field in the tube 15 which is as uniform as possible. A uniform distribution of the magnetic field is a necessary condition in order to get a constant sensitivity of the system over the whole cross-sectional area of the tube.

The system will become almost independent of the way the metallic particle follows through the field. When the latter would not be uniform — at least to a certain degree — the sensitivity of the system would show too great fluctuations depending on whether the particle passes through the center of the magnetic field or through an area situated more closely to the periphery of it, in our example, the wall of the tube 15.

A configuration of a detector coil assembly creating a sufficiently uniform magnetic field is represented in FIG. 2. Instead of only providing a self-induction coil 14 (here represented in sectional view), which would create a magnetic field of non-uniform distribution, inside the tube 15 and out, field correcting expedients have been provided.

To this end, bars 17 of a ferrite composition parallelly oriented in axial direcion of the tube are provided at the outer periphery of the self-induction coil 14 in order to concentrate the lines of magnetic force 16, so that these lines are primarily directed towards the inner space of the self-induction coil 14. A further improvement consists in providing a short circuiting ring 18 around the outer periphery of the coil 14 and the bars 17. This ring is made of a highly conductive material, preferably copper or brass. In so doing, the reluctance of the space outside of said ring 18 becomes very high, because occasional lines of force which would encircle said ring would generate an electric current in the latter, which itself produces a field annihilating the field created by said lines of force.

A final correction of the field may be obtained by the provision of bars 19 made of highly conducting material in the inner periphery of the self-induction coil 14 and in axial direction of the tube 15. In this way, a more or less analogous phenomenon as that described in the foregoing paragraph occurs, which causes the lines of force 16 to find a path going over and under the upper respectively the lower end of said bars 19. In this way, a relatively uniform magnetic field is obtained in the horizontal section of the tube 15, due to the fact that the ratio between the longest lines of magnetic force (passing through the center) and the shortest lines of magnetic force (those passing in close proximity of the bars 19) is strongly reduced and amounts to only 1.5 to 2 instead of 10 and more. So, the very high concentration of the magnetic field in the vicinity of the oil 14 is annihilated.

In order to amplify this favourable effect, it is advantageous to distribute the windings of the self-induction coil 14 as equally as possible over the height of the coil. This is not always very easy, since the number of windings, necessary to obtain the required self-inductance is rather limited.

A solution therefor is represented in FIG. 3, which consists is putting a plurality of coils 14 in parallel, so that a relatively long combined coil is obtained, whereas the coefficient of self-induction L may be kept as low as desired.

In FIG. 4 is represented a schematic diagram of the electronic circuit in an apparatus according to the invention.

The electronic circuit 10 comprises a parallel resonant circuit, built-up by capacitors 21a and 21b and the self-induction coil 14 (provided with the field correcting expedients shown in FIG. 2 and built-up as illustrated in FIG. 3), the latter being inductively coupled with a second self-induction coil 22, serving as the link of the parallel resonant circuit with the oscillator 23. Also other types of coupling arrangements e.g. capacitive or galvanic types of coupling may be applied at will. The parallel resonant circuit is connected with the buffer stages 24 and 25, which may e.g. be emitter-followers and which will act as the input stages of two channels for further processing of the oscillator signal.

The first channel converts the sinusoidal signal generated in the parallel resonance circuit into a block shaped one by means of the trigger 26. Said signal 31 (FIG. 7) is forwarded towards one input of a digital frequency or phase discriminator 29, the function of which will be further described hereinafter.

The second channel too, converts the sinusoidal signal of the oscillator 23 into a block shaped one 32 (see FIG. 7) by means of the trigger 28, but a supplementary phase shifting circuit 27 is provided which will shift the input signal over 90 degrees. The circuit 27 is composed of the coupling capacitor 35 and the inductively coupled coils 34 and 36, as may be seen in FIG. 5.

The outputs of the triggers 26 and 28 are fed to the input section of the discriminator 29, the output signal of which may be used to energize an alarm circuit (not shown) after amplification by means of an amplifier 30.

Where the second channel is concerned, which at resonant frequency delivers a signal having a 90° phase difference with the signal of the first channel, a phase shift of $90° \pm \Delta\phi$ is obtained, when the oscillator frequency will change to $f \pm \Delta f$ due to the presence of the foreign metallic particle.

The sensitivity of the phase difference detecting action will depend on the so-called quality factor of the resonant circuit, formed by the coil 14 and the capacitors 21a and 21b. FIG. 6 shows the relation between the phase shift difference ($\Delta\phi$) and the function of the frequency ($f$). Defining this phase difference equal to 90° at resonant frequency $f_o$ curves 50, 51 and 52 show the variation in phase difference for respectively a high, a moderate and a low quality factor of the resonant circuit. It may be derived from this figure that a high quality factor will give the best results as to the sensitivity of the system. Indeed, the higher the quality factor Q, the smaller will be the minimum size of the particles to be detected.

Referring now to FIGS. 7a and 7b, the building-up of a signal 33 at the exit of the discriminator 29 is considered.

In FIG. 7a the situation is illustrated which corresponds with the parallel resonant circuit at resonant frequency, which means that no metallic particle is in the vicinity of the self-induction coil, the latter being positioned around the tube wherethrough the flow of polymer particles passes.

The curve marked 31 is the output signal of the first channel generated at the exit of the trigger 26 and has the same phase as the oscillator signal, that is to say, they both pass through zero at the same time. The curve 32 is the output signal of the second channel, generated at the exit of the trigger 28 and which lags by 90° behind said first signal.

When both signals 31 and 32 are fed to the discriminator 29, the latter having digital multiplication properties, an output signal 33 is generated. Indeed, assuming that the input signals 31 and 32 vary pulsewise between +1 and −1 Volts, the signal 33 too will vary between said two values, although the frequency will be doubled. This last feature however is without significance. The characteristic feature, however, is that the average value 37 of said signal 33 will be zero, as the surfaces of the curve 33 lying above and under the zero-axis are equal to each other, so that the positive values cancel out negative ones.

From the foregoing one may thus conclude, that when no foreign particle is present in the vicinity of the detecting coil 14 (FIG. 1) no signal at the output stage of the circuit appears and the associated alarm device (not shown) is not energized.

When, on the contrary, a disturbance of the homogeneous magnetic field in the coil 14 (FIG. 1) occurs, caused by the presence of a metallic particle in the flow of polymer chips or granulate, the frequency and amplitude of the voltage in the parallel resonant circuit will be submitted to variations. Consequently, the frequency of the output signals will be subjected to variations too while simultaneously, the phase of the signal of the second channel will alter. This situation is represented in FIG. 7b.

Curve 31 represents the block-shaped output signal of the first channel varying between, say +1 and −1 Volt. In the second channel the output signal 32 is obtained the phase shifting of which will be different from 90°, depending on the fact that the resonant circuit formed by the coil 14 and the capacitors 21a and 21b (FIG. 4) will behave as an inductive or a capacitive circuit. The frequency of the block shaped signal 32, however, will be the same as that obtained in the first channel, as both signals are derived from the same source without frequency division or multiplication in either of the channels.

In the example, represented in FIG. 7b, it will be assumed that the signal 32 lags by less than 90°. The discriminator unit 29 in FIG. 4 will in this case generate an output signal which is no longer equal to zero. Indeed, multiplication of both signals 31 and 32 results in a surface of the curve 33 above the zero level which is greater than that below it. In the case represented, this results in a value of the voltage output voltage 37, situated between 0 and +1 Volts. After amplificaion, this signal may act to energize an alarm circuit.

The aforegoing reasoning may be applied in the case that the signal 32 lags by more than 90° behind the signal 31. Then, an average output voltage 37, lying between 0 and −1 Volts will be built-up.

FIG. 8 represents a schematic view of the oscillator 23. The oscillating stage itself comprises the transistor 46 which acts according to the common emittor principle in class C permitting a relatively high power amplification.

A new problem, however, is created in this way, by the fact that the period during which the transistor is conductive, becomes relatively small, causing a rise of the distortion of the signal. This phenomenon can only be limited by providing a loose coupling between the self-induction coils 14, 22 and 38 or by adding a supplementary self-induction 39 in the collector circuit of the transistor 46. Preferably, the circuit formed by the capacitor 48 and the self-inductions 22 and 39 is chosen in such a way that the resonant frequency of this circuit is identical with the resonant frequency of the parallel network formed by self-induction coil 14 and capacitors 21a and 21b. Consequently, the energy conversion from a pulse-shaped signal into a sinusoidal one occurs in the series resonant circuit (capacitor 48, self-induction coils 22 and 39), and not in the proper oscillator itself. The control signal which will be used for further processing in both mentioned channels is taken at the common point of capacitors 21a and 21b and may be applied first at the input stage of a voltage follower prior to be split.

From the foregoing, one may conclude that the oscillator acts according to the class C principle, the advantage being that a relatively high yield is obtained, but having the inconvenience that the generated signal shows a fairly high distortion. The parallel resonant circuit, however, is driven in class A so that distortion is greatly reduced. The class C bias for the oscillator stage may be optimized by the adequate choice of the values of capacitors 43 and 44. The doide 41 permits an easy starting of the oscillator because during the starting period it is in cut-off condition, so that the current flowing through the resistor 40 is fully injected into the base of transistor 46. When the oscillator is in full working condition, however, diode 41 is conductive and part of the current goes through resistor 42, so that the injected current in the base of the transistor is lowered.

The oscillator circuit according to FIG. 8 is advantageously mounted in completely screened boxes in order to eliminate occasional parasitic signals of and/or interferences from outside sources. The influence of mechanical vibrations may be reduced by providing the electronic circuitry as close as possible to the detector circuit, thus renouncing the use of long cable connections between both. The presence of small quantities of water in the polyester granulate and/or chips had no significant influence upon the detection capacity of the system.

In each of the FIGS. 9, 10 and 11 the length of the X-axis is a measure for the diameter of the coil.

A series of curves, respectively for iron, stainless steel, brass, aluminium and copper are presented in FIGS. 9a to 9e for the case that only a self-induction coil is provided as detection system and when a resonant frequency of 200 kHz is used. The background noise component of the signal is fairly high, whereas no reproducible signal over the diameter of the coil can be obtained.

FIGS. 10a to 10e show the detection response curves for the respective materials at a resonant frequency of 100 kHz, when simultaneously optimizing the distribution of the windings of the detector coil. In this case, already reproducible results are obtained as a function of the coil diameter, but the ratio between the signals obtained at the periphery and those near the middle of the coil is still too great. The background noise, however has decreased considerably.

Finally, FIGS. 11a to 11e illustrate the curves for respectively the same materials when applying a resonant frequency of 100 kHz, optimizing the distribution of the windings of the detector coil and using a detector configuration as presented in FIG. 1. From these curves, it may be derived that a good quality signal enabling a faultless detection of commonly used metals, is obtained.

From the foregoing, one may conclude that an adequate detection apparatus for proving the presence of metallic particles in a dielectric medium has been devised. In use, the apparatus shows a good reliability, and small metallic particles may be detected, even when the latter pass through the center of the tube wherethrough the dielectric flows. Moisture does not give rise to a parasitic signal, so that the alarm circuit is solely energized when a real danger for the extrusion line occurs.

The apparatus may be completed and/or adapted for other techniques, such as for example the detection of metallic particles in polymeric webs, when passing the latter through a coil of adequate shape, without departing from the scope and spirit of the invention. If desired, in such an application of the invention, or in any other application thereof, the tube such as tube 15 in FIG. 1, can be dispensed with provided the dielectric material is caused or constrained to follow a path through the self-induction coil. The invention includes any apparatus as herein defined, with such modification. When testing a web for example, the web can easily be guided, e.g. by rollers, so as to follow a path through the said coil.

We claim :

1. An apparatus for detecting the presence of metallic particles within a flowing dielectric medium, comprising a tube through which the dielectric medium is caused to flow, oscillator means oscillating at a given resonant frequency, a parallel resonant circuit excited by the electrical energy emitted by said oscillator means and producing a sinusoidal output signal, said parallel resonant circuit having a self-induction coil arranged around said tube, means for receiving the sinusoidal output signal from said circuit and producing two separate parallel sinusoidal signals, means for shaping said sinusoidal signals into separate square wave signals and for shifting one of said square wave signals 90° out of phase with the other such signal, and discriminator means to which said first and second square wave signals are applied and capable of delivering a constant amplitude output signal having an average value equal to zero when no metallic particle in the flow of said dielectric medium is present and proportionate to the displacement of said square wave signals from said 90° phase difference when a particle is detected in said flow.

2. Apparatus according to claim 1, in which the resonant frequency of the parallel resonant circuit is the same as that of said oscillator means.

3. Apparatus according to claim 1, in which the state of resonance of said parallel resonant circuit and of said oscillator means corresponds with the condition of absence of particles in the tube.

4. Apparatus according to claim 1, in which said oscillator means and said resonant circuit are inductively coupled with each other.

5. Apparatus according to claim 4, in which the inductive coupling occurs by the intermediary of the tube through which the dielectric medium flows.

6. Apparatus according to claim 1, in which first and second square wave signals have the same frequency as that of said oscillator means.

7. Apparatus according to claim 1, in which the frequency of said oscillator means amounts to 100 kilo Hertz.

8. Apparatus according to claim 1, in which said parallel resonant circuit has a high quality factor.

9. Apparatus according to claim 1 in which means are provided to create an homogeneous magnetic field within the self-induction coil of said parallel resonant circuit and the interior of the said tube around which it is concentrically arranged.

10. Apparatus according to claim 9, in which said homogeneous magnetic field is obtained by providing highly conducting members inside said self-induction coil.

11. Apparatus according to claim 10, in which said highly conducting members are in the form of bars which are circumferentially arranged around the tube following the axial direction of the latter in mutually spaced relation.

12. Apparatus according to claim 11, in which said bars are made of copper.

* * * * *